United States Patent
Pecor et al.

(10) Patent No.: US 6,398,782 B1
(45) Date of Patent: Jun. 4, 2002

(54) BIPOLAR VASCULAR SEALING APPARATUS AND METHODS

(75) Inventors: Robert Pecor, Irvine; Timothy C. Mills, Belvedere Tiburon; Howard Taymor-Luria, Belvedere; Clifford E. Currier, Aliso Viejo; Mark A. Konno, Laguna Beach; Charles R. Mooney, Costa Mesa; David J. Evans, Irvine; Luchy D. Roteliuk, Lake Forest, all of CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 08/440,624

(22) Filed: May 15, 1995

Related U.S. Application Data (63) Continuation-in-part of application No. 07/959,337, filed on Oct. 13, 1992, now Pat. No. 5,415,657.

(51) Int. Cl.[7] ............................................. A61B 18/14
(52) U.S. Cl. .............................. 606/50; 606/46; 606/48
(58) Field of Search ............. 606/45–50; 607/100–104; 604/21

(56) References Cited

U.S. PATENT DOCUMENTS

| 3,176,114 A | | 3/1965 | Kneisley |
| 3,301,258 A | * | 1/1967 | Werner et al. ................ 606/50 |
| 3,613,682 A | | 10/1971 | Naylor |
| 3,699,967 A | | 10/1972 | Anderson |
| 3,801,800 A | | 4/1974 | Newton |
| 3,874,388 A | | 4/1975 | King et al. |
| 3,920,021 A | * | 11/1975 | Hiltebrandt ................... 606/50 |
| 3,963,030 A | | 6/1976 | Newton |
| 4,043,342 A | * | 8/1977 | Morrison, Jr. ................ 606/50 |
| 4,269,174 A | | 5/1981 | Adair |
| 4,424,833 A | | 1/1984 | Spector et al. |
| 4,532,924 A | * | 8/1985 | Auth et al. ................... 606/50 |
| 4,685,459 A | | 8/1987 | Koch et al. |
| 4,878,493 A | * | 11/1989 | Pasternak .................... 606/48 |
| 4,929,246 A | | 5/1990 | Sinofsky |
| 5,026,367 A | * | 6/1991 | Leckrone et al. ............. 604/21 |

(List continued on next page.)

FOREIGN PATENT DOCUMENTS

| DE | 36 32 197 A1 | 3/1988 |
| DE | 38 38 840 A1 | 5/1990 |
| EP | 0 275 642 A1 | 7/1988 |
| FR | 2 594 322 | 8/1987 |
| WO | WO 93/21844 | 11/1993 |
| WO | WO 94/08513 | 4/1994 |
| WO | WO 94/24948 | 11/1994 |

OTHER PUBLICATIONS

Brochure for VasoSeal™ from Datascope, 1991.

*Primary Examiner*—David M. Shay
(74) *Attorney, Agent, or Firm*—Guy Cumberbatch; Lena Vinitskaya (57) ABSTRACT

The method, device and system for electrical sealing of a puncture opening in a blood vessel wall. In a first embodiment, a vascular sealing probe has two bipolar electrodes formed thereon, is insertable to a position whereat the bipolar tip is adjacent the blood vessel puncture site to effect electrocauterization or electrocoagulation of the puncture site. In a second embodiment the bipolar vascular sealing probe has a first electrode formed thereon and an electrode-guide wire has the second bipolar electrode formed thereon. The electrode-guide wire is passable through a lumen formed in the probe such that the second electrode on the electrode-guide wire is positioned close enough to the first electrode positioned on the probe to permit electrical current to pass therebetween.

15 Claims, 9 Drawing Sheets

U.S. PATENT DOCUMENTS

| | | |
|---|---|---|
| 5,044,375 A | 9/1991 | Bach, Jr. et al. |
| 5,057,105 A | 10/1991 | Malone et al. |
| 5,108,421 A | 4/1992 | Fowler |
| RE33,925 E | 5/1992 | Bales et al. |
| 5,156,613 A | 10/1992 | Sawyer |
| 5,158,561 A | 10/1992 | Rydell et al. |
| 5,188,634 A | 2/1993 | Hussein et al. |
| 5,226,908 A | 7/1993 | Yoon |
| 5,336,222 A | 8/1994 | Durgin, Jr. et al. |
| 5,366,443 A * | 11/1994 | Eggers ......................... 606/31 |
| 5,383,876 A | 1/1995 | Nardella |
| 5,403,311 A | 4/1995 | Abele et al. |
| 5,403,312 A | 4/1995 | Yates et al. |
| 5,415,657 A | 5/1995 | Taymor-Luria |
| 5,437,664 A | 8/1995 | Cohen et al. |
| 5,443,481 A | 8/1995 | Lee |
| 5,499,981 A * | 3/1996 | Kordis ......................... 606/41 |
| 5,507,744 A * | 4/1996 | Tay et al. ..................... 606/46 |

* cited by examiner

BIPOLAR VASCULAR SEALING APPARATUS AND METHODS

RELATED APPLICATION

This patent application is a continuation-in-part of U.S. patent application Ser. No. 07/959,337, entitled Percutaneous Vascular Sealing Apparatus and Method, filed Oct. 13, 1992, now U.S. Pat. No. 5,415,657. The entire disclosure of the U.S. patent application Ser. No. 07/959,337 is hereby expressly incorporated herein by reference.

FIELD OF THE INVENTION

The present invention relates generally to medical devices and methods, and more particularly to a device and method for sealing a puncture site in a blood vessel wall.

BACKGROUND OF THE INVENTION

In modern medical practice, many clinical procedures require that a catheter or other device be percutaneously inserted into a blood vessel. Such clinical procedures include; diagnostic cardiac catheterization, percutaneous translumenal angioplasties or atherectomies, etc. In many of these procedures, the catheter or other device is typically inserted into the blood vessel by a technique known as the "Seldinger Technique".

In accordance with the Seldinger Technique, a hollow bore needle is initially inserted into a blood vessel, such as the femoral artery, and a guide wire is subsequently advanced through the lumen of the needle into the blood vessel. The needle is then retracted, leaving the guide wire in place. Thereafter, a tubular introducer having a tapered dilator extending therethrough, is advanced over the guide wire and into the blood vessel. The tapered distal end of the dilator protrudes out of and beyond the distal end of the introducer, to slowly dilate the blood vessel puncture site to a size which is large enough to receive and allow passage of the introducer sheath. The guide wire and dilator are subsequently withdrawn, leaving the introducer sheath in place within the blood vessel. A catheter scope or other device is then passed through the introducer sheath and advanced through the vasculature to its desired location.

After the procedure has been completed, the catheter, scope, or other device and tubular introducer are extracted and removed from the puncture site. Direct pressure is customarily applied to the puncture site to maintain hemostasis, and to minimize hematoma formation. Despite such routine application of direct pressure to the puncture site following the procedure, some localized bleeding, bruising or hematoma formation often occurs. Additionally, other complications, such as pseudoaneurysm formation, may also occur.

The prior art has included a number of methods and devices which are purported to be capable of sealing a vascular puncture site following removal of the percutaneously inserted introducer or the like. For example, one product known by the trade name VASOSEAL™ (Datascope Corporation, Montvale, N.J.) comprises a bolus of collagenous material which is passed through an introducer into the vicinity of the blood vessel puncture site. The deployment of the collagenous material near the blood vessel puncture site is intended to promote coagulum formation, and resultant sealing of the blood vessel puncture site.

Additionally, devices for sealing of blood vessel wall punctures have been described in U.S. Pat. No. 4,829,994 (Kurth), U.S. Pat. No. 4,929,246 (Sinofsky), U.S. Pat. No. 4,744,364 (Kensey) and U.S. Pat. No. 5,108,421 (Fowler).

Also, U.S. patent application Ser. No. 07/959,337 (Taymor-Luria), of which this Application is a continuation-in-part, describes an electrosurgical blood vessel sealing probe which is insertable through a vascular sheath and subsequently retractable to a point where the distal tip of the probe is in contact with blood vessel wall puncture site. Thereafter, electrical energy is applied through the probe to effect electrocauterization or electrocoagulation of the blood vessel wall puncture site. The probe incorporates a guiding means to enhance the operator's ability to precisely position the distal tip of the probe in its intended position adjacent the blood vessel wall puncture site.

The present invention is directed to bipolar embodiments of the blood vessel sealing probe and method described in parent application Ser. No. 07/959,337 (Taymor-Luria), of which this application is a continuation-in-part.

SUMMARY OF THE INVENTION

This continuation-in-part patent application is directed to inventions which comprise bipolar embodiments of a blood vessel sealing probe of the general type disclosed in U.S. patent application Ser. No. 07/959,337. Also, this patent application is directed to methods and apparatus for facilitating operative positioning of a blood vessel sealing device at a location which is immediately adjacent, or at a specific spaced distance from, a blood vessel wall puncture site.

A first embodiment of a bipolar blood vessel sealing probe of the present invention generally comprises an elongate probe or catheter body having a bipolar electrode tip on the distal end thereof, and a bipolar connector on the proximal end thereof. In this embodiment, the bipolar connector is connectable to an electrical power source to provide a flow of electrical current from the connector to the bipolar electrode tip. A guide wire lumen may extend through at least a portion of the probe body, to facilitate advancement of the probe over a pre-inserted guide wire.

A second embodiment of a bipolar blood vessel sealing probe with the present invention generally comprises an elongate probe or catheter body having a single electrode at or near its distal end, and a guide wire which extends longitudinally therethrough so as to protrude out of and beyond the distal end of the probe or catheter body. The region of the guide wire immediately adjacent the distal end of the probe or catheter body forms a second bipolar electrode. Both the guide wire and the elongate probe or catheter body are connectable to an electrical power source to provide a flow of electrical current to the electrode located on the probe or catheter body and the electrode located on the guide wire. In this regard, the electrode located on the probe or catheter body and the electrode located on the guide wire combine to form a bipolar electrode tip whereby electrical energy passes between the probe or catheter body and the guide wire. The guide wire may remain fully or partially inserted into the blood vessel wall puncture so as to facilitate bipolar electrocauterization or electrocoagulation of the blood vessel wall puncture site.

Further in accordance with the invention, the bipolar blood vessel sealing probes of the above-summarized first and second embodiments are useable in combination with an electrical power source. The electrical power source preferably comprises a radio frequency alternating current generator. Because the bipolar probe of the present invention is capable of operating with minimal power, the electrical power source may be preset or limited so as to deliver radio frequency alternating current at power levels below 20 watts, and preferably about 1–10 watts. Additionally, it is preferable that the electrical power be delivered through the probe for discrete periods of time effective to produce electrocauterization or electrocoagulation of the blood vessel wall, while avoiding thermal damage or degradation to the blood vessel wall and/or surrounding tissue. In this regard, a timer may be provided to limit the individual periods of electrical current to approximately 30 seconds–60 seconds each. Additionally, or alternatively, a temperature sensor and feedback control apparatus may be utilized to decrease or terminate the electrical current flowing through the probe when the temperature at the distal end of the probe reaches a predetermined limit.

Further in accordance with the invention, there is provided a non-electrically-conductive guide wire which is usable in connection with the first embodiment of the bipolar blood vessel sealing probe.

Still further in accordance with the invention, there is provided an electrically-conductive electrode-guide wire which is usable with the second embodiment of the bipolar blood vessel sealing probe, said electrically conductive electrode-guide wire forms a second electrode adjacent the distal end of the probe or catheter body, as summarized hereabove with respect to the second embodiment.

Still further in accordance with the invention there are provided methods of sealing puncture sites in blood vessel walls using the bipolar probes and systems of the present invention. In general, the first embodiment of the bipolar blood vessel sealing probe of the present invention may be utilized by positioning the distal end of the probe or catheter body adjacent the blood vessel puncture site and passing electrical current to the bipolar electrode tip so as to effect bipolar electrocauterization or electrocoagulation of the blood vessel puncture site. In contrast, the second embodiment of the bipolar blood vessel sealing probe may be used by a method whereby the distal end of the probe or catheter body is positioned adjacent the outer surface of the blood vessel puncture site and the electrically conductive guide wire is permitted to protrude at least partially through the blood vessel wall puncture site. Thereafter, the electrical current is passed through the probe or catheter body and the electrically conducive guide wire so as to effect bipolar electrocoagulation of the blood vessel puncture site.

Still further in accordance with the invention, a sheath or shield formed of insulating material, such as PTFE (Teflon™) may be positioned about all or a portion of either the first or second embodiment of the bipolar blood vessel sealing device of the present invention to prevent sticking of the bipolar electrode(s) to the surrounding tissue and/or burning of such surrounding tissue.

Still further in accordance with the invention, there are provided apparatus and methods for positioning or locating the distal end of a vascular sealing probe or device at a position immediately adjacent to, or at a specific spaced distance from, a blood vessel wall puncture site. In general, the preferred apparatus for positioning the distal tip of the probe comprises a notch or depression formed in the outer surface of the probe, at a known distance from the distal tip thereof. As the probe is withdrawn, in the proximal direction, through a blood vessel wall puncture site, the blood vessel wall will elastically engage the notch or depression thereby resulting in increased resistance to further proximal withdrawal. Upon noting such increased resistance, the operator is thereby informed that the probe need only be further withdrawn by a distance equal to the known distance between the notch and the distal end of the probe body. Accordingly, when the increased resistance is noted, the operator may utilize additional pulling force to overcome such increased resistance and, thereafter, to further withdraw the probe in the proximal direction by a distance equal to the known distance between the locator notch and the distal end of the probe body, thereby ensuring that the distal end of the probe body is then positioned immediately adjacent the blood vessel wall puncture site. Alternatively, various other types of apparatus may be utilized to sense the passage of the distal end of the probe out of the blood vessel lumen or to otherwise sense or determine the correct position of the distal end of the probe so as to facilitate positioning of the distal end of the probe at an intended location immediately adjacent to, or a specific spaced distance from, the blood vessel wall puncture site. Examples of such alternative apparatus include, but are not necessarily limited to, a) a bleed back tube or lumen which opens at or near the distal end of the probe to permit visual verification of blood return such that, when the distal end of the probe is extracted from the lumen of the blood vessel, such blood return will cease, b) an electrical impedance measuring apparatus which senses the difference in impedance between the blood vessel wall and the surrounding tissue, c) a flow meter at the distal tip of the probe to determine when the distal tip of the probe is no longer in contact with the flow of blood passing through the blood vessel, d) a thermistor or temperature measuring apparatus operative to sense when dissipation of heat produced by the flowing blood has ceased, thereby indicating when the sensor-site of the thermistor or temperature measuring device has exited lumen of the blood vessel, e) a piezoelectric apparatus operative to determine differences in the electrical potential of the blood, blood vessel wall or tissue surrounding the blood vessel, thereby facilitating determination of when the distal end of the probe has been extracted from the lumen of the blood vessel, and f) an optical apparatus (e.g., a laser) operative to optically discern or determine the type of matter (e.g., blood, vascular wall, connective tissue) which is adjacent an optical sensor located at or near the distal end of the probe.

Further objects and advantages of the invention will become apparent to those skilled in the art upon reading and understanding of the following detailed description, and the accompanying drawing.

DETAILED DESCRIPTION OF PREFERRED EMBODIMENTS

The following detailed description and the accompanying drawings are provided for purposes of describing and illustrating presently preferred embodiments of the invention only, and are not intended to limit the scope of the invention in any way.

A. First Embodiment Having Both Bipolar Electrodes Located on Probe Body

With reference to FIGS. 1–8, the first embodiment of the vascular sealing system of the present invention generally comprises a first embodiment of a bipolar vascular sealing probe 10 which is connectable to a electrical power unit 18.

i. The Device of the First Embodiment

Figure 1:
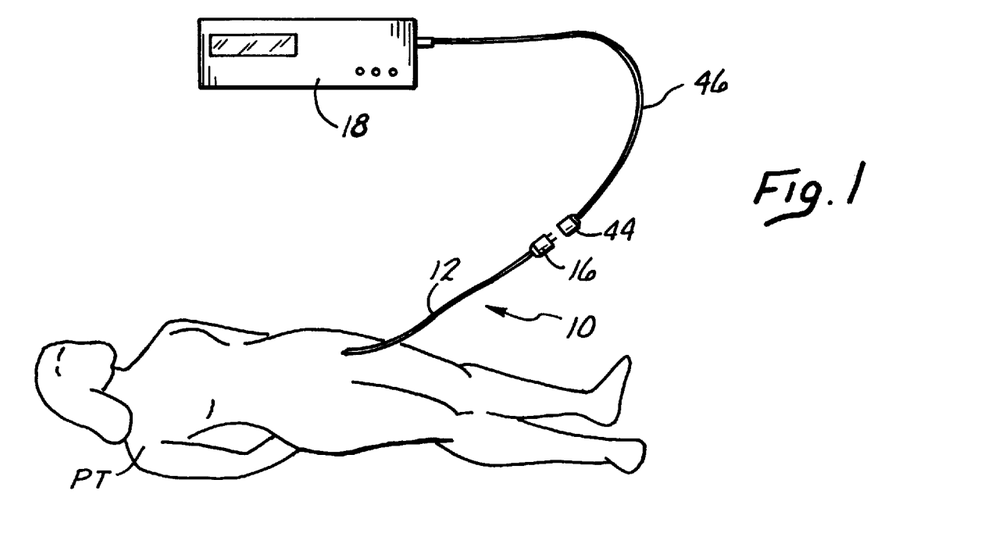
FIG. 1 is a perspective view of a first embodiment of a bipolar vascular sealing system in accordance with the present invention.
Figure 2:
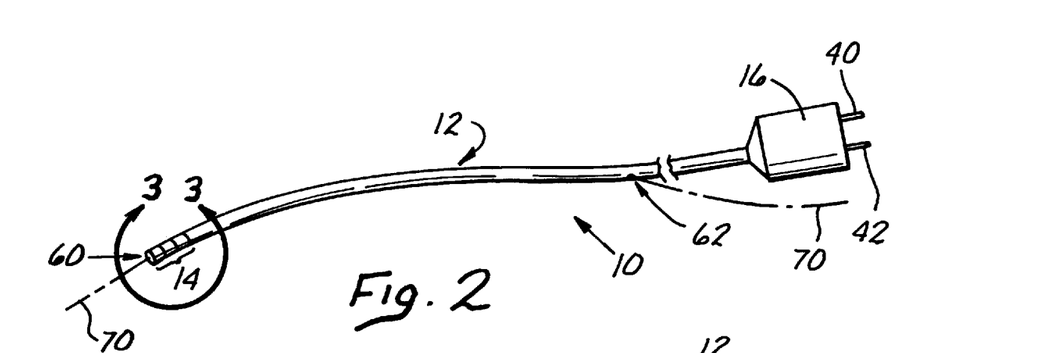
FIG. 2 is a perspective view of the first embodiment of the bipolar vascular sealing probe of FIG. 1.

The first embodiment of the bipolar vascular sealing probe 10 preferably comprises an elongate probe body 12, a bipolar electrode tip 14 on the distal end of the probe body 12 and a proximal connector 16 on the proximal end of the probe body 12.

The proximal connector 16 is directly or indirectly connectable to the electrical power unit 18 which is operative to pass current through the probe 12 to the bipolar distal tip 14 situated on the distal end of the probe 12. In the embodiment shown, a cable 46 extends from the power unit 18 and terminates in a receptacle 44 which is connectable to the proximal connector 16 of the probe 10.

Figures 4, 7:
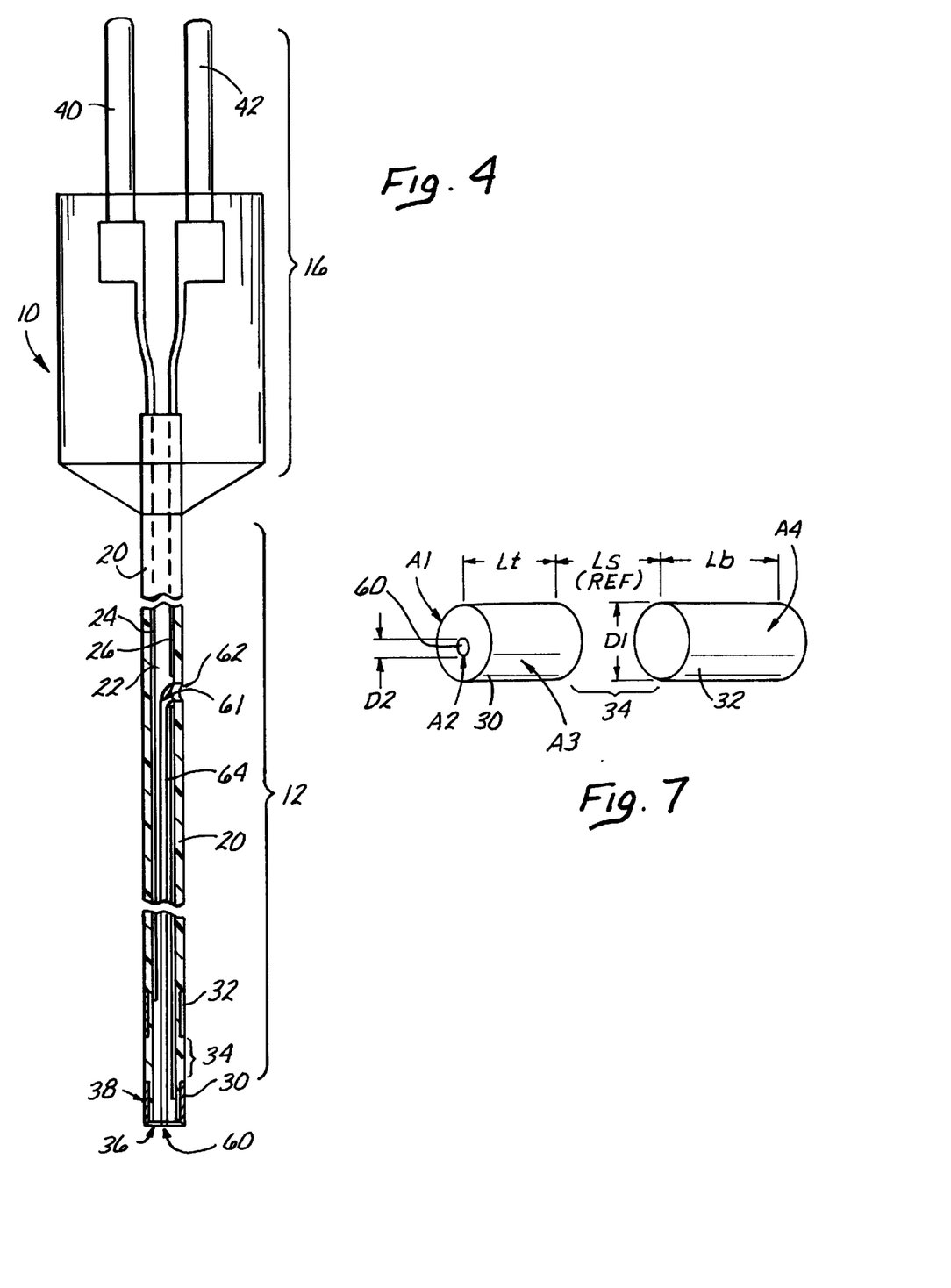
FIG. 4 is an enlarged longitudinal sectional view of the first embodiment vascular sealing probe of FIG. 2.
FIG. 7 is a schematic showing of the bipolar electrode tip of a first embodiment of the vascular sealing probe of the present invention.

The probe body 12 preferably comprises an elongate pliable catheter or sheath 20 which extends distally from the proximal connector 16. The sheath 20 is preferably formed of polyethylene or other suitable plastic material. A hollow lumen 22 extends longitudinally through the pliable sheath 20 and serves to contain various internal components of the probe 10 as described more fully herebelow.

Figure 3:
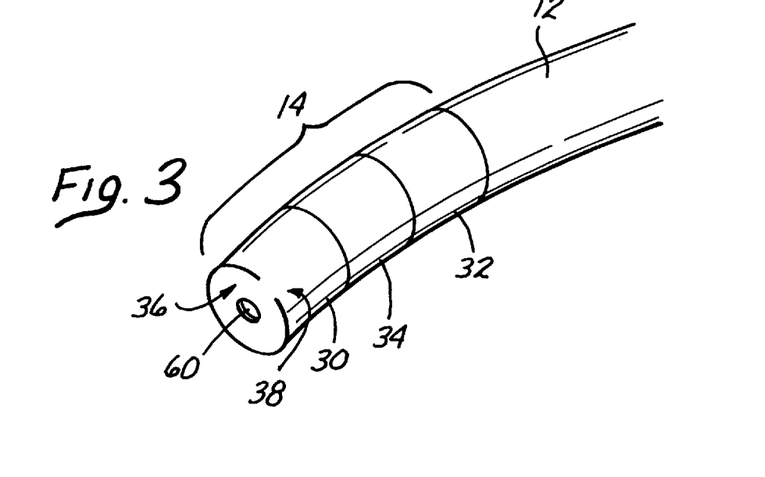
FIG. 3 is an enlarged perspective view of the distal portion of the first embodiment vascular sealing probe shown in FIG. 2.

The bipolar electrode tip 14 on the distal end of the probe 10 preferably comprises a distal electrode 30, a proximal electrode 32 and a non-conductive region such as a band of electrically insulative material 34 disposed between the distal electrode 30 and the proximal electrode 32. In the embodiment shown, the distal electrode 30 is a cap-like member formed of metal or other electrically conducted material and mounted on the distal end of the tubular sheath 20. As such, the distal electrode 30 incorporates a distal or frontal surface 36 and a generally cylindrical sidewall 38. The distal-most portion of the tubular sheath 20 is downturned to a reduced diameter which is approximately equal to or slightly greater than the inner diameter of the cap-like distal electrode to facilitate mounting of the cap-like distal electrode 30 on the distal end of the sheath 20, as shown. By such arrangement, the outer diameter of the cap-like distal electrode 30 is substantially the same as the outer diameter of the pliable tubular sheath 20.

Also, in the first embodiment shown, the proximal electrode 32 comprises a cylindrical band of metal or other electrically conductive material mounted about the outer surface of the tubular sheath 20. A portion of the outer surface of the tubular sheath 20 is downturned to receive the band-like proximal electrode 32 thereon. By such arrangement, the outer diameter of the band-like proximal electrode 32 may be substantially equivalent and continuous with the outer diameter of the tubular sheath 20, as shown.

The electrically insulative band 34 between the distal electrode 30 and proximal electrode 32 may comprise a separate band of plastic or other electrically non-conductive material. Alternatively, such electrically insulative band 34 may comprise a portion (e.g., a raised or protruding area) of the electrically insulative tubular sheath 20 disposed between the distal electrode 30 and proximal electrode 32.

In the first embodiment, it may sometimes be preferable that the outer surface area of the distal electrode 30 be approximately the same as the outer surface area of the proximal electrode 32 to avoid concentration of energy in either electrode 30, 32. In other instances, it may be desirable for one electrode 30, 32, to have a greater surface area than the other electrodes 30, 32, to purposely cause greater concentration of energy, and thus more heating, in the region of only one of the electrodes 30, 32. In this regard, the relative surface areas of the cap-like distal electrode 30 and the band-like proximal electrode 32 may be calculated using the specific equation shown below FIG. 7 of this patent application.

$D1 := .105 \text{ in} \quad L_{total} := .33 \text{ in}$
$D2 := .025 \text{ in} \quad Ls = .11 \text{ in}$ Input variables $A1 := \pi \times (D1^2/2) \quad A1 = 0.009 \text{ in}^2$ $A2 := \pi \times (D2^2/2) \quad A2 = 4.909 \times 10^{-4} \text{ in}^2$ $A3 = D1 \times \pi \times Lt$ $A4 = D1 \times \pi \times Lb$ Since the total surface area of the tip must be equal to the total surface area of the band:

$St = (A1 - A2)/A3 \qquad\qquad Sb = A4$
$St = Sb$
$A3 - A4 = A2 - A1$
$Lt - Lb = (A2 - A1)/(D1 \times \pi)$
$Lb + Ls - Lt = 3 \text{ in}$
$L_{metal} = L_{total} - Ls \qquad\qquad L_{metal} = 0.22 \text{ in}$
$Lt - Lb = L_{metal}$
$Lb = L_{metal} - Lt$
$Lt - L_{metal} - Lt = (A2 - A1)/D1 \times \pi$
$Lt = (1/2) \times (L_{metal} \times D1 \times \pi - A2 - A1)/(D1 \times \pi) \quad Lt = 0.0976 \text{ in}$
$Lb = L_{metal} - Lt \qquad\qquad Lb = 0.1224 \text{ in}$ First and second electrical conduction members, such as wires 24, 26, extend longitudinally through the probe body 12 to facilitate passage of electrical current from the proximal connector 16 to the bipolar electrode tip 14 situated on the distal end of the probe 12. In the embodiment shown, the first electrical conduction wire 24 extends longitudinally through the lumen 22 of the sheath 20 and is connected, at its distal end, to proximal electrode 32. Similarly, a second electrical conduction wire 26 extends through the lumen 22 and is connected at its distal end, to distal electrode 30. The proximal ends of the first and second electrical conduction wires 24, 26 extend into proximal connector 16, and are separately coupled to first and second connector pins 40, 42. The pins 40, 42 of proximal connector 16 are sized and configured to insert into the corresponding receiving receptacle 44 of a cable 46 which is connected to the radio frequency electrical current generator 18. The cable 46, including the receiving receptacle 44, may be of the type commercially available as Item No. 60-5135-001, from Aspen Laboratories, Englewood, Colo. By such arrangement, electrical current from the radio frequency current generator device 18 will pass through cable 46, and into pin electrodes 40 and 42 of proximal connector 16. Current passing into pin electrode 40 will subsequently pass through the first conductor wire 24 to proximal electrode 32. Current passing into pin electrode 42 will subsequently pass through second conductor wire 26 to distal electrode 30.

The electrical power unit 18 preferably comprises a wall outlet powered or battery powered radio frequency alternating current generator device. One such device is commercially available as the Cameron-Miller Model 5200 radio frequency electrosurgical generator Cameron-Miller, Chicago, Ill. The current required to operate the preferred bipolar probe 10 is no greater than 20 watts and preferably approximately 1–10 watts over a maximum time duration of 1 minute. Accordingly, in view of this relatively low current requirement, the power unit 18 my comprise a small handheld, battery powered radio frequency generator capable of delivering 1–10 watt output for the desired time periods (e.g., 30 seconds or 1 minute). Such battery powered power unit 18 may be rechargeable when not in use.

The power unit 18 or associated components within the system may also incorporate a timer operative to automatically terminate each period of power output after a predetermined time (eg. 30 seconds or 1 minute). Alternatively or additionally, the system may incorporate a temperature sensor at or near the bipolar electrode tip 14 of the probe 10 and a feedback control apparatus which will automatically attenuate (i.e., lower or terminate) the power output when the temperature at the electrode tip 14 has reached a predetermined limit. The inclusion of such timer and/or temperature feedback control apparatus may serve to prevent overheating or thermal degradation of the blood vessel wall or adjacent tissue.

In the first embodiment, it is preferable that the probe 10 incorporate a guide wire lumen which extends longitudinally through at least a portion of the probe body 12 to facilitate advancement of the probe 10 over a pre-inserted guide wire. In the embodiment shown in FIGS. 2–6, a "monorail" type guide wire lumen is provided, wherein a first guide wire passage aperture 60 is formed in the distal face 36 of the cap-like distal electrode 30 and a second guide wire passage aperture 62 is formed on the sidewall of the sheath 20, at a preferred distance of approximately 20 cm from the distal end of the probe 10. A guide wire tube 64 extends longitudinally through the lumen 22 of sheath 20, between the first guide wire passage aperture 60 and second guide wire passage aperture 62. By such arrangement, the lumen 65 of the guide wire tube 64 forms a direct channel between first guide wire passage aperture 60 and second guide wire aperture 62.

It will be appreciated that, as an alternative to the "monorail" type guide wire passageway shown in the figures, an "over-the-wire" type of guide wire passageway may also be employed, wherein the second guide wire passage aperture is situated at the proximal end of the probe 10 (e.g., in the proximal connector) and the guide wire passage lumen extends substantially through the entire length of the probe body 12.

ii. Optional Insulating Sleeve to Shield Adjacent Tissue

Figure 5A:
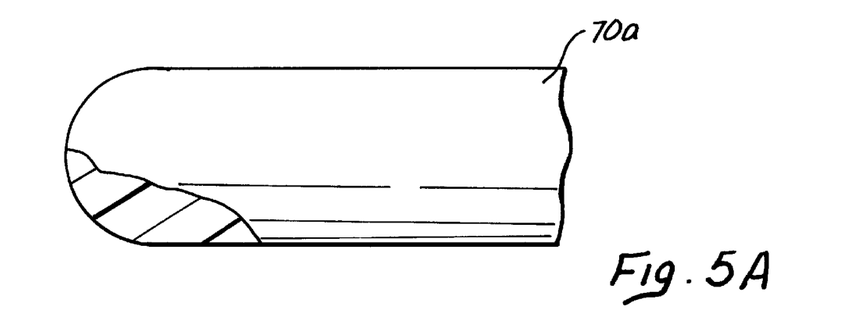
FIG. 5a is a cut-away side elevational view of a distal portion of a of a non-electrically-conductive guide wire optionally useable in conjunction with the first embodiment of the present invention.
Figure 5B:
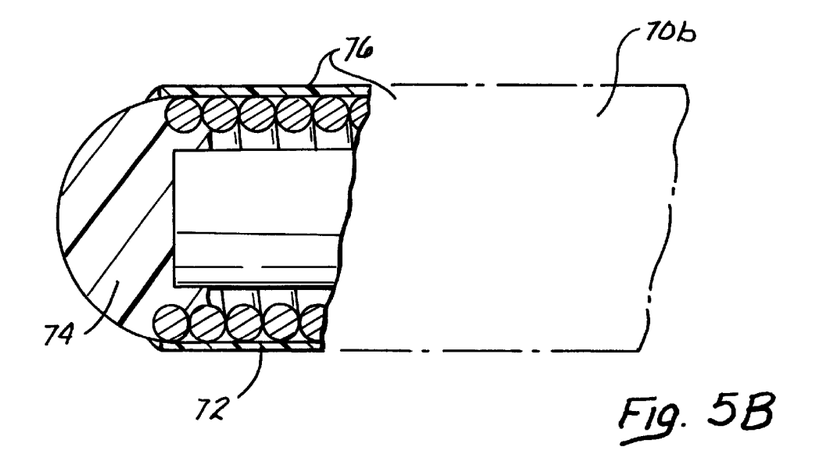
FIG. 5b is a cut-away side elevational view of a distal portion of an alternative configuration of a non-electrically-conductive guide wire optionally useable in conjunction with the first embodiment of the present invention.
Figure 5C:
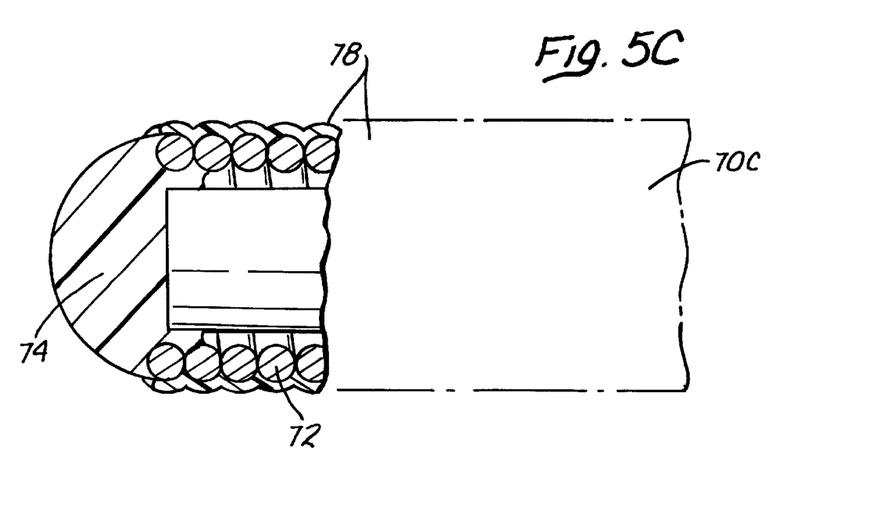
FIG. 5c is a cut-away side elevational view of a distal portion of another alternative configuration of a nonelectrically-conductive guide wire useable in conjunction with the first embodiment of the present invention.

Optionally, a cylindrical sleeve or shield formed of polytetrafluoroethylene (Teflon®) or other suitable insulating material my be mounted about the lateral or sidewall surface of the bipolar electrode tip 14 to prevent the electrodes 30, 32 and/or insulating band 34 from sticking to the adjacent muscle, adipose or connective tissue. The distal surface 36 of the distal electrode 30 will remain unshielded, so as to directly contact the blood vessel wall puncture site when the probe 10 is in its preferred operative position (see FIGS. 6d and 6e).

iii. Optional Guide Wire Formed of Insulating Material for Use with First Embodiment It will be appreciated that, if the bipolar probe tip 14 is to be energized while a guide wire 70 extends through the probe 12, it may be advantageous for the guide wire 70 to be formed of electrically insulative material so as not to conduct current from the distal and/or proximal electrodes 30, 32 of the probe 12. In this regard, the present invention may include a guide wire formed at least partially of electrically insulative material. FIGS. 5a–5c show three alternative guide wire constructions wherein electrically insulated materials are utilized.

As shown in FIG. 5a, there is provided a guide wire 70a formed entirely of plastic or other non-electrically-conductive material. In this regard, the plastic body of the guide wire 78 may be formed or extruded of plastic material having the suitable non-conductivity properties.

FIG. 5b shows an alternative guide wire 70b comprising a continuous wire coil 72, a solid distal tip plug 74 and a non-electrically-conductive covering or sheath 76 disposed on the outer surface of the guide wire 70b and fully covering the electrically conductive wire coil 72. Such outer covering or sheath 76 may comprise a cylindrical tube of plastic material or other suitable electrically non-conductive material.

FIG. 5c shows yet another alternative guide wire 70c comprising a continuous wire coil 72, a solid distal tip plug 74, and a non-electrically-conductive coating 78 disposed on the outer surface of the guide wire 70c fully covering the electrically conductive wire coil 72. Such surface coating 78 may comprise a plastic coating or other non-conductive coating which is initially applicable to the outer surface of the guide wire in a liquid form, and which subsequently dries or cures to a substantially solid coating composition.

It will be appreciated that the use of a non-conductive or insulative guide wire 70 may not be necessary in embodiments wherein the guide wire tube 64 is sufficiently insulative to prevent current from passing from the electrodes 30, 32 into a conductive guide wire 70 disposed within the lumen 65 of the guide wire tube 64.

iv. A Preferred Method of Using the First Embodiment

Figures 6A, 6B, 6C:
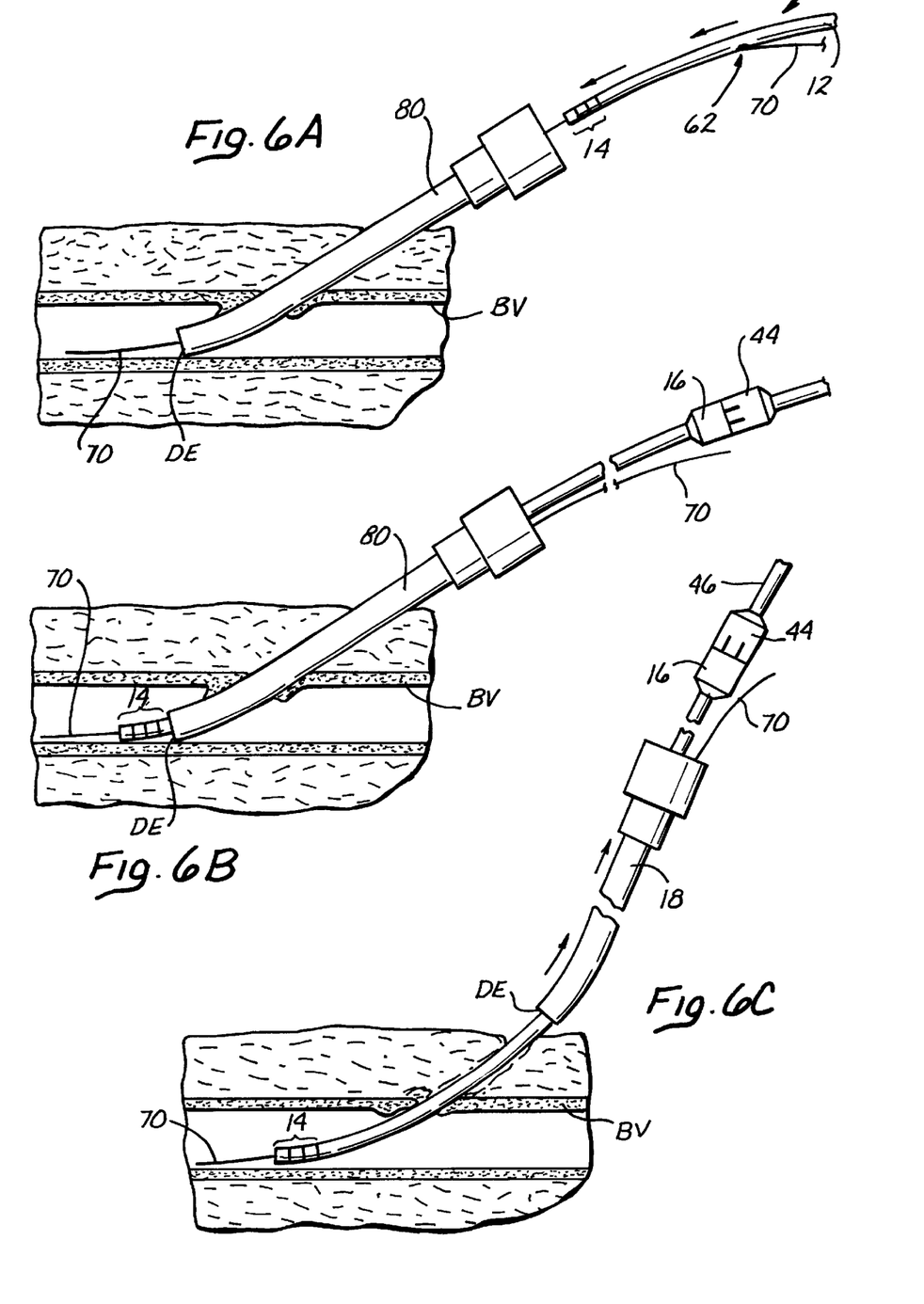
FIGS. 6a–6f is a step-by-step illustration of a method for utilizing the first embodiment of the present invention.

A preferred method of using the bipolar probe device 10 is shown in step-wise fashion in FIGS. 6a–6f. As shown, a tubular introducer 80 is emplaced within a blood vessel BV, by the above-described Seldinger Technique. The tubular introducer 80 extends through a tract formed within the skin and subcutaneous tissue, as well as through a puncture site PS formed in the wall of the blood vessel BV. A guide wire 70 extends through the lumen of the introducer 80, into the blood vessel BV. The proximal end of the guide wire 70 is inserted into the first guide wire aperture 60 in the distal end of the probe 10. The probe 10 is then advanced over the guide wire 70, through the lumen of the introducer 80, and into the blood vessel BV. As the probe 10 is advanced, the proximal end of the guide wire 70 will emerge out of the second guide wire passage aperture 62, as shown in FIG. 6a.

The advancement of the probe 10 continues until the distal portion of the probe body 12 has emerged out of the distal end DE of the introducer 80, within the lumen of the blood vessel BV also, the proximal connector of the probe 10 is inserted into the receiving receptacle 44 of cable 46 so as to couple the probe 10 to the radio frequency power unit 18. (FIG. 6b)

Thereafter, the introducer 80 is retracted in the proximal direction to a point where the distal end DE of the introducer 80 is withdrawn from the blood vessel BV, and such that the distal tip of the probe body 12 protrudes out of the distal end DE of the introducer 80. The distal portion of the probe body 12, and the guide wire 70, remain inserted within the lumen of the blood vessel BV. (FIG. 6c)

Figures 6D, 6E:
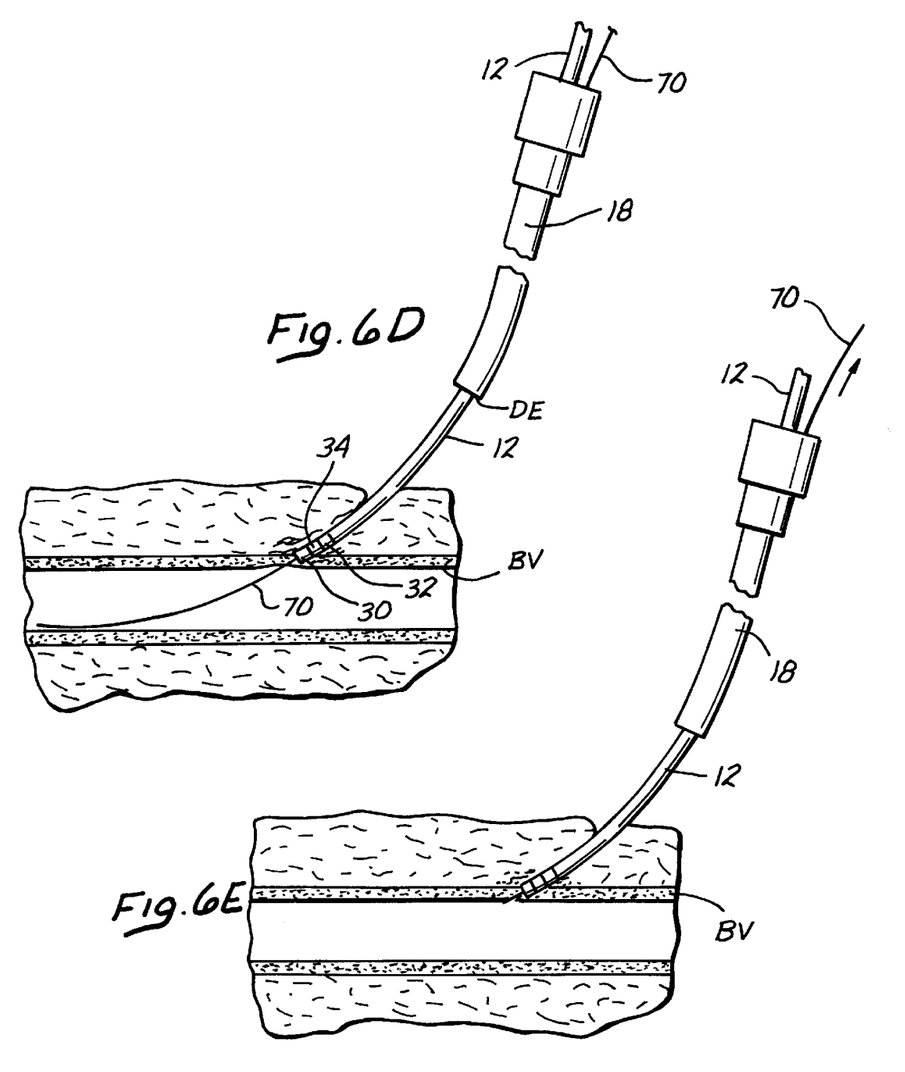

Thereafter, the probe 10 is withdrawn in the proximal direction until the distal end of the probe body 12 has been retracted through the puncture site in the wall of the blood vessel BV. A "snap" is typically felt by the operator when the distal end of the probe body 12 passes through the wall of the blood vessel BV. At this point, retraction of the probe 10 is stopped and the probe 10 is maintained in a substantially fixed longitudinal position, such that the bipolar electrode tip 14 on the distal end of the probe body 12 will remain positioned immediately adjacent the puncture site in the blood vessel wall. With the guide wire 70 remaining emplaced within the lumen of the blood vessel BV, an initial period of electrical current, preferably radio frequency alternating current, is passed from the power unit 18, through cable 46, through the probe 10 and to the bipolar electrode tip 14. Such passage of electrical current to the distal electrode 30 and proximal electrode 32 of the bipolar tip 14 causes the surrounding tissue, and the adjacent blood vessel wall puncture site, to undergo electrocauterization or electrocoagulation. Such electrocauterization or electrocoagulation of the blood vessel wall and/or adjacent tissues will effect an initial closure or seal of the blood vessel wall puncture site. (FIG. 6d)

Thereafter, the guide wire 70 is withdrawn through the probe 10 in the proximal direction, such that the distal end of the guide wire 70 becomes fully retracted into the probe body 12, or completely withdrawn from the probe device 10. After the guide wire 70 has been so retracted, a second period of electrical current is passed from the power unit 18, through the probe device 10 to further cauterize, coagulate or seal the wall of the blood vessel BV. This second period of electrical current serves to seal any small opening in the blood vessel wall through which the guide wire 70 had previously passed. (FIG. 6e)

Figure 6F:
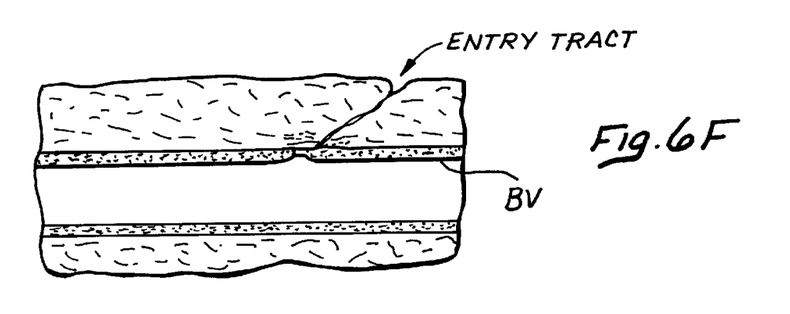

Thereafter, the probe device 10 is fully retracted from the entry tract, and removed. The electrocauterization or electrocoagulation of the blood vessel wall effected by the probe device 10 has served to fully seal the puncture site in the blood vessel wall, thereby preventing significant hemorrhaging from the blood vessel BV into the adjacent entry tract or surrounding tissues. (FIG. 6f)

v. Alternative Tip Configurations for First Embodiment

Figure 8A:
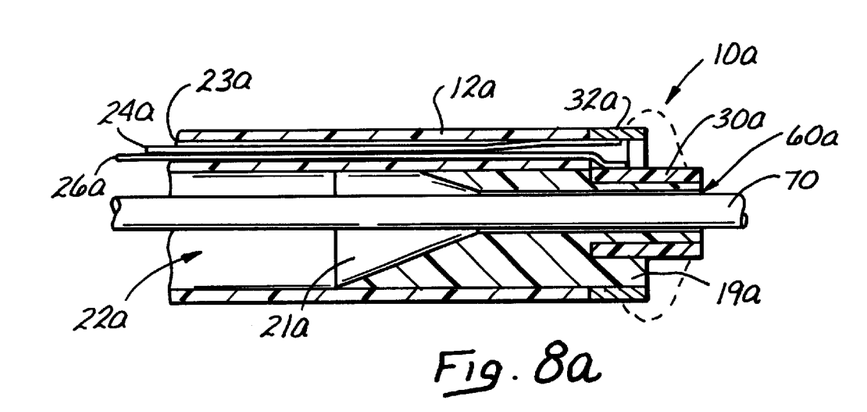
FIG. 8a is a partial longitudinal sectional view of an alternative configuration of the distal end of a bipolar vascular sealing probe of the first embodiment of the present invention.
Figure 8B:
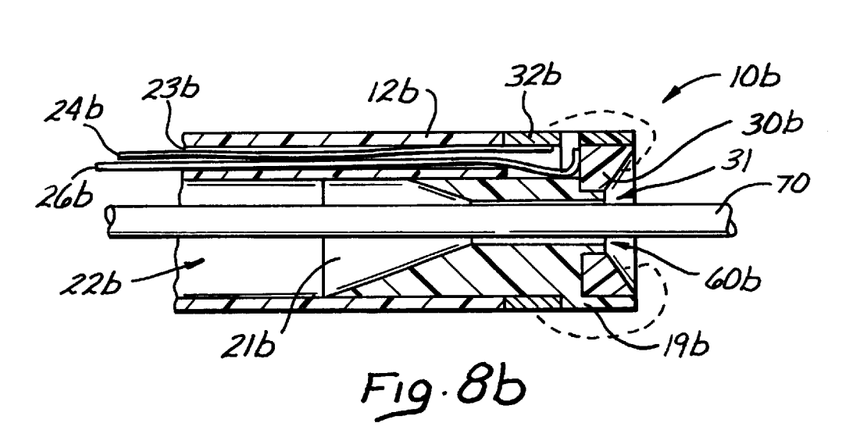
FIG. 8b is a partial longitudinal section view of another alternative configuration of the distal end of a bipolar vascular sealing probe of the first embodiment of the present invention.
Figure 8C:
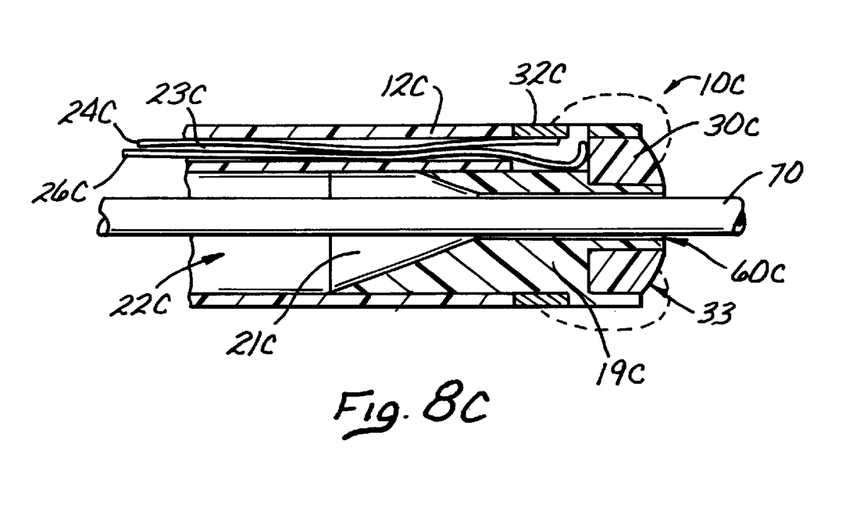
FIG. 8c is a partial longitudinal sectional view of another alternative configuration of the distal end of a bipolar vascular sealing probe of the first embodiment of the present invention.

FIGS. 8a–8c show alternative distal tip configurations for the vascular sealing probe 10 of the first embodiment of the present invention.

With reference to FIG. 8a, an alternative configuration of the probe 10a wherein the probe body 12a comprises an elongate, pliable dual lumen catheter having a first lumen 22a and a second lumen 23a. A first electrical conduction wire 24a and a second electrical conduction wire 26a extend longitudinally through the second lumen 23a and are connected, at their distal ends, to the proximal electrode 32a and distal electrode 30a, respectively. An electrically insulative plug member 19a is inserted into the distal end of the probe body 12a. The plug member 19a has a central guide wire passage bore or aperture 60a extending longitudinally therethrough. A tapered or frusto conical region 21a is formed on the proximal end of the guide wire passage aperture 60a to facilitate location and entry of the distal end of the guide wire into the guide wire passage aperture 60a. In the embodiment shown in FIG. 8a, the proximal electrode 32a comprises an electrically conductive band formed about the distal end of the probe body 12a, and the distal electrode 30a comprises a smaller diameter, cylindrical electrode protruding from the central of the distal end of the probe body 12a, as shown. In this regard, the protruding distal electrode 30a may be permitted to protrude slightly into the vascular wall puncture site such that, when electrical current passes between the proximal electrode 32a and distal electrode 30a, there will result effective electrocoagulation or electrocauterization of the blood vessel wall puncture site.

With reference to FIG. 8b, there is shown an alternative configuration of the vascular sealing probe 10b wherein the probe body 12b comprises a dual lumen catheter or tube having a main or guide wire passage lumen 22b and a second lumen 23b. First and second electrical conduction wires 24b, 26b extend longitudinally through the second lumen 23b of the probe body 12b and are connected, at their distal ends to the proximal electrode 32b and distal electrode 30b, respectively. An electrically insulative plug member 19b is inserted into the distal end of the probe body 12b. A guide wire passage bore or aperture 60b extends longitudinally through the plug member 19b. A tapered or frusto conical region 21b is formed on the proximal end of the guide wire passage bore or aperture 60b to facilitate location and passage of the distal end of the guide wire 70 through the guide wire passage aperture 60b. The proximal electrode 32b comprises an electrically conductive band formed about the outer surface of the probe body 12b near the distal end thereof. The distal electrode 30b comprises an electrically conductive annular body positioned within the distal end of the probe body 12b and having a concave or otherwise indented distal surface 31 in this regard, electrical energy will pass from the outer surface of the proximal electrode 30b to the concaved or indented distal surface 31 of the distal electrode 30b, as indicated by the dotted lines on FIG. 8b. Thus, when the distal end of the probe 10b is positioned immediately adjacent the outer surface of a vascular wall puncture site, the concaved or indented distal face 31 of the distal electrode 30b will serve to localize or concentrate the electrical energy passing between the bipolar distal 32b and proximal 30b electrodes, thereby effecting localized or concentrated electrocoagulation or electrocauterization of the blood vessel wall puncture site.

FIG. 8c shows yet another alternative configuration of the vascular sealing probe 10c wherein the probe body 12c comprises a dual-lumen catheter or sheath having a first guide wire lumen 22c and a second lumen 23c first 24c and second 26c electrical conduction wires extend longitudinally through the second lumen 23c and are connected, at their distal ends, to the proximal electrode 32c and distal electrode 30c, respectively. An electrically insulative plug member 19c is positioned within the distal end of the probe body 12c. A guide wire passage bore aperture 60c extends longitudinally through the plug member 19c. A tapered or frusto conical region 21c is formed in the proximal end of the guide wire passage bore or aperture 60c to facilitate location and passage of the distal end of the guide wire 70 through the guide wire passage aperture 60c. The proximal electrode 32c comprises an electrically conductive band formed about the outer surface of the probe body 12c near the distal end thereof. The distal electrode 30c comprises an annular member inserted into the distal end of the probe body 12c and having a convex or outwardly protruding distal surface 33. When electrical energy is passed through the first and second electrical conduction members 24c 26c, such electrical energy will subsequently pass between the outer surface of the proximal electrode 32c and the convex or outwardly extending frontal surface 33 of the distal electrode 30c as indicated by the dotted lines in FIG. 8c. In this regard, the convex or outwardly extending frontal surface 33 of the distal electrode 30c will facilitate location of the electrical energy in a region of tissue surrounding the convex or outwardly protruding frontal surface 33 of the distal electrode 30c, thereby facilitating the desired electrocoagulation or electrocauterization of the blood vessel wall puncture site when the distal end of the probe 10c is positioned adjacent thereto.

B. A Second Embodiment Having One Bipolar Electrode Located on Probe Body and a Second Bipolar Electrode Located on Electrode-Guide Wire FIGS. 9–13 are directed to a second embodiment of the present invention wherein one of the bipolar electrodes is positioned on a guide wire, and the other is positioned on the probe or catheter body.

i. The Device of the Second Embodiment

Figure 9:
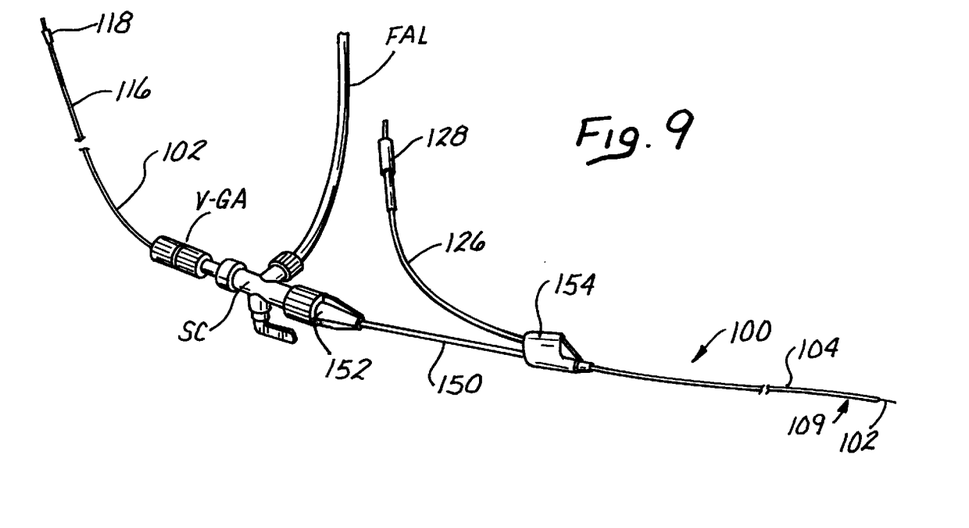
FIG. 9 is a perspective view of a second embodiment of a bipolar vascular sealing system in accordance with the present invention.

A preferred example of a bipolar vascular sealing system of the second embodiment of the invention is shown in FIG. 9. With reference to FIG. 9, the system comprises a vascular sealing probe 100 in combination with an electrode-guide wire 102.

Figure 10:
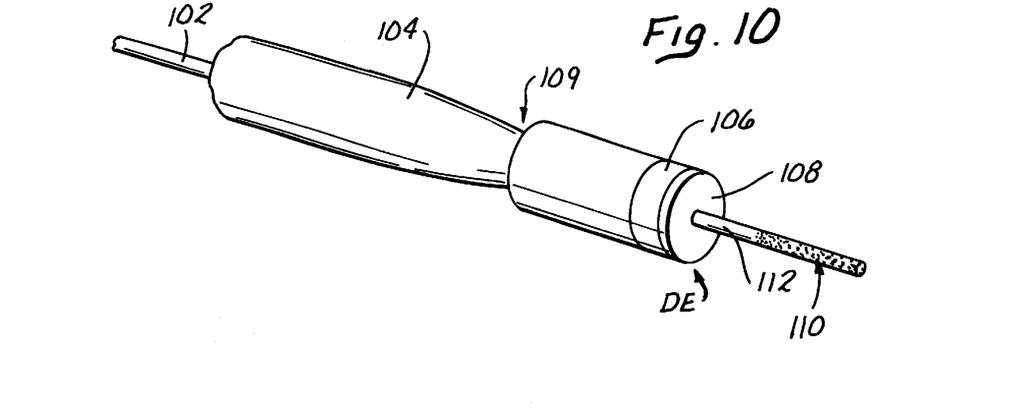
FIG. 10 is an enlarged perspective view of the distal end of the second embodiment of the bipolar system of the present invention shown in FIG. 9.
Figure 11:
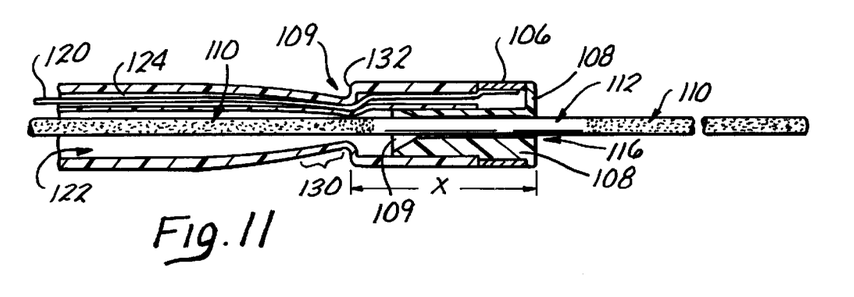
FIG. 11 is a longitudinal sectional view through line 11—11 of FIG. 10.

The vascular sealing probe 100 comprises an elongate pliable catheter or probe body 104 having a first or proximal bipolar electrode 106 formed on the outer surface thereof, near the distal end thereof. The first or proximal bipolar electrode 106 comprises an electrically conductive member, such as a cylindrical band of metal, positioned about the outer surface of the probe body 104, adjacent the distal end DE thereof. An electrically insulative plug 108 is inserted into and affixed to the distal end of the probe body 104 such that the peripheral portion of the insulative plug 108 forms an insulative spacer between the proximal electrode 106 and the distal face of the probe body 104.

The electrode-guide wire 102 preferably comprises an elongate guide wire formed of an electrically conductive material and having an insulative coating 110 disposed on the proximal and distal regions thereof, with an uncoated or exposed region 112 remaining therebetween. A lead wire 116 having a connector 118 formed thereon extends from the proximal end of the electrode-guide wire 102 to permit connection of the electrode-guide wire 102 to an attendant electrical signal generation device.

In the preferred embodiment shown, the probe body 104 comprises an elongate, pliable dual-lumen tube or catheter having a first lumen 122 and a second lumen 124. A proximal electrode wire 120 extends through the second lumen 124 and is connected to the proximal electrode 106. A lead wire 126 and connector 128 extend from the proximal end of the proximal electrode wire 124. The connector 128 is connectable to an attendant electrical signal generation device such that electrical current may pass from the signal generation device to the first or proximal bipolar electrode 106 located on or near the distal end of the probe body 104.

In the second embodiment shown in FIG. 9, a plastic encasement member 154 is positioned on the proximal end of the probe body 104 and forms a graspable enclosure for the interconnection of the lead wire 126 to the probe body 104. A proximal tube 150 extends from encasement member 154. The proximal tube 150 has an inner lumen extending longitudinally therethrough and is continuous with the first lumen 122 of the probe device 100, through which the electrode-guide wire 102 is inserted. A Leur connector 152 is formed on the proximal end of the proximal tube 150. In typical usage, a separate stop cock SC is connected to Leur connector 152. A fluid administration line FAL is connected to one side arm of the stock cock SC, and a valving-gripping apparatus V-GA is positioned to the other side arm of the stock cock SC. The valving-gripping apparatus V-GA may comprise any suitable type of hemostasis valving member operative to prevent backflow of blood through the lumen 122 of the probe body 104 and proximal tube 150, and also operative to permit passage of the electrode-guide wire 102 therethrough. Such valving-gripping apparatus V-GA is preferably further operative to be tightenable about the electrode-guide wire 102 to hold the electrode guide wire 102 in a substantially fixed longitudinal position relative to the probe body 104. This is typically accomplished by tightening the opposing portions of the valving-gripping apparatus V-GA so as to cause an internal gripping member, such as an O-ring, to fictionally engage the outer surface of the electrode-guide wire 102 as it extends therethrough. Examples of valving-gripping apparatus V-GA usable for this purpose include commercially available product nos. 190-5017a and 190-5014a, marketed by Medical Disposables International West Conshocken, Pa.

ii. Locator Apparatus Usable to Facilitate Accurate Positioning of the Probe

The second embodiment shown in FIGS. 9–13 includes a locator notch 109 formed in the outer surface of the probe body 104, at a known distance X from the distal end DE of the probe body 104. This locator notch 109 may be of any suitable configuration, and preferably comprises a proximally tapered region 130 which extends from and is immediately adjacent to an annular abutment shoulder 132, said annular abutment shoulder 132 comprising an annular ridge which is substantially perpendicular to the longitudinal axis LA of the probe body 104, and which is a known distance X from the distal end DE of the probe body 104. As described in more fully herebelow, this locator notch 109 is usable as an indicator that the probe body 104 has been withdrawn to a position which is said known distance X from the distal end DE from the probe body 104. In this regard, further withdrawal of the probe in proximal direction by the known distance X will result in accurate positioning of the distal end DE of the probe body 104, immediately adjacent the blood vessel puncture site which is to be treated. It will be appreciated that the utility of the locator notch 109 is not limited to the second embodiment of the invention shown in FIGS. 9–13, but may also be incorporated into and used in conjunction with the first embodiment of the invention shown in FIGS. 1–8, and/or any other vascular catheter or vascular sealing probe wherein it is desirable to accurately position the distal end of the catheter probe immediately adjacent the vascular puncture site through which said catheter or probe is inserted.

Alternatively, various other types of apparatus may be utilized to sense the passage of the distal end of the probe out of the blood vessel lumen or to otherwise sense or determine the correct position of the distal end of the probe so as to facilitate positioning of the distal end of the probe at an intended location immediately adjacent to, or a specific spaced distance from, the blood vessel wall puncture site. Examples of such alternative apparatus include, but are not necessarily limited to, a) a bleed back tube or lumen which opens at or near the distal end of the probe to permit visual verification of blood return such that, when the distal end of the probe is extracted from the lumen of the blood vessel, such blood return will cease, b) an electrical impedance measuring apparatus which senses the difference in impedance between the blood vessel wall and the surrounding tissue, c) a flow meter at the distal tip of the probe to determine when the distal tip of the probe is no longer in contact with the flow of blood passing through the blood vessel, d) a thermistor or temperature measuring apparatus operative to sense when dissipation of heat produced by the flowing blood has ceased, thereby indicating when the sensor-site of the thermistor or temperature measuring device has exited lumen of the blood vessel, e) a piezoelectric apparatus operative to determine differences in the electrical potential of the blood, blood vessel wall or tissue surrounding the blood vessel, thereby facilitating determination of when the distal end of the probe has been extracted from the lumen of the blood vessel, and f) an optical apparatus (e.g., a laser) operative to optically discern or determine the type of matter (e.g., blood, vascular wall, connective tissue) which is adjacent an optical sensor located at or near the distal end of the probe.

iii. A Preferred Method of Using the Second Embodiment

The preferred method of utilizing the vascular sealing probe 100 of the second embodiment of the present invention is illustrated in FIGS. 12a–12d. As shown, the probe body 104 is initially inserted into the blood vessel BV such that the locator notch 108 is positioned within the lumen of the blood vessel and the distal portion of the electrode-guide wire 102 extends out of and beyond the distal end of the probe body 104.

Figure 12A:
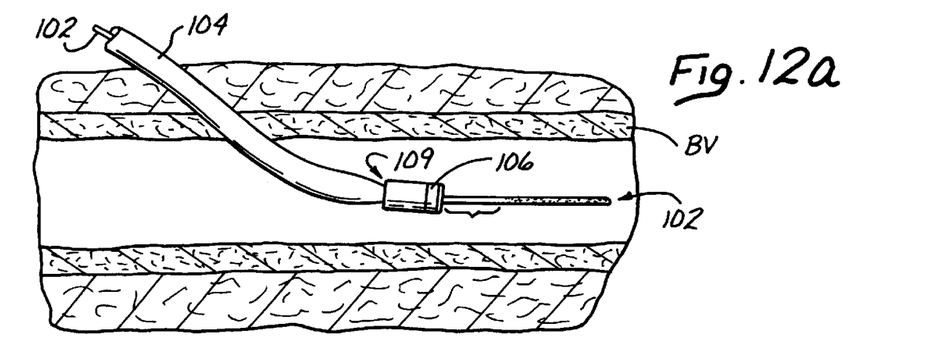
FIGS. 12a–12d is a step-by-step illustration of a method for utilizing the second embodiment of the present invention.
Figures 12B, 12C:
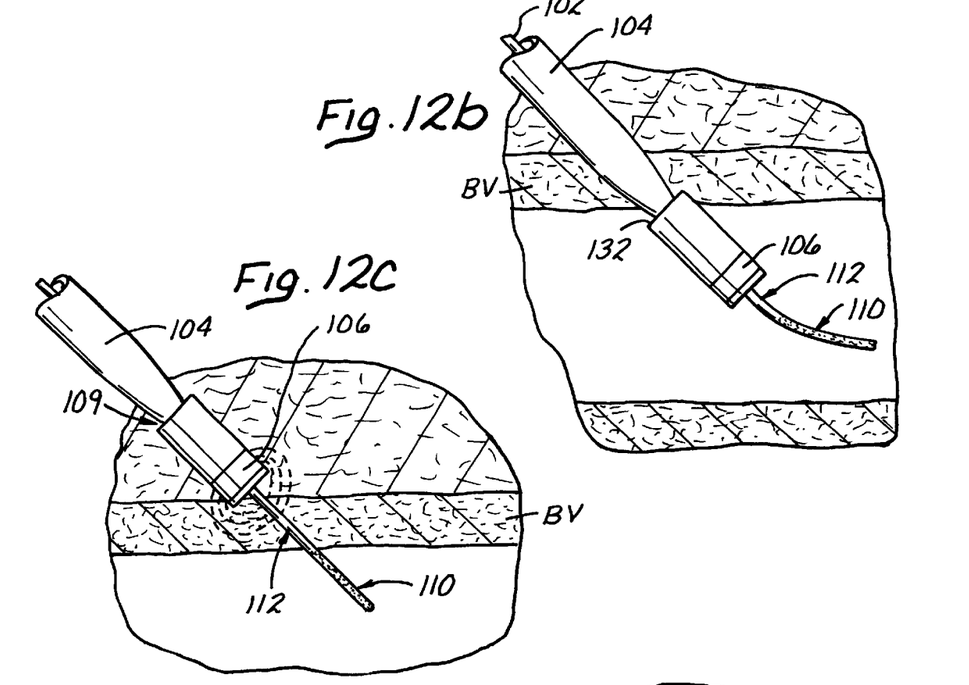
Figure 12D:
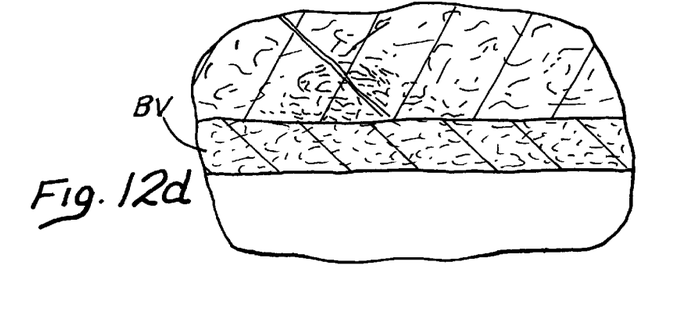

As shown in FIG. 12b, the probe body 104 is then retracted in the proximal direction until the elasticity of the wall of the blood vessel BV closes around the proximal tapered region 130 of the locator notch 108, thereby causing the abutment shoulder 132 of the notch 108 to engage the blood vessel wall. Such engagement of the shoulder 132 against the blood vessel wall will result in notable resistance to further proximal withdrawal of the probe body 104, thereby indicating to the operator that the present position of the probe is a known distance X from a point where the distal end of the probe will be immediately adjacent the wall of the blood vessel BV.

As shown in FIG. 12c, the operator will then apply additional pulling force to the probe body 104 to further retract the probe in the proximal direction by a distance approximately equal to the known distance X from the abutment shoulder 132 to the distal end of the probe. This may be facilitated by distance measurement marks on the outer surface of the probe body 104. After the probe 100 has been retracted to such location wherein the distal end of the probe is immediately adjacent the puncture site in the blood vessel wall BV, the guide wire may be retracted or manipulated such that the non insulated region 112 of the guide wire extends through the puncture site within the blood vessel wall BV, but the distal insulated region 110 of the electrode-guide wire 102 extends into the lumen of the blood vessel BV. Thereafter, with the electrode-guide wire plug 118 and the proximal electrode plug 128 inserted into an appropriate electrical signal generator, electrical current, preferably alternating current, is passed to the proximal electrode 106 and the non-insulated region 112 of the electrode-guide wire 102, thereby causing electrical current to pass therebetween as indicated by the dotted lines in FIG. 12c. The passage of the current between the proximal electrode 106 and the non-insulated region 112 of the electrode guide wire 102 results in electrocoagulation or electrocauterization of the blood vessel wall puncture site and/or the connective tissue or space immediately on the outer surface thereof.

As shown in FIG. 12b, the probe 100 and electrode-guide wire 102 are then retracted and removed. As shown in FIG. 12b, the puncture site in the wall of the blood vessel BV has been substantially sealed or cauterized so as to prevent leakage of blood from the lumen of the blood vessel BV into the surrounding tissue.

It will be appreciated that the electrical signal generator, power and current settings usable with this second embodiment of the probe 100 are the same as those articulated and referred to hereabove with respect to the first embodiment of the probe 10.

iv. Alternative Tip Configurations For Second Embodiment

FIGS. 13a–13d show alternative configurations for the distal end of the vascular sealing probe 100 of the second embodiment of the present invention.

Figure 13A:
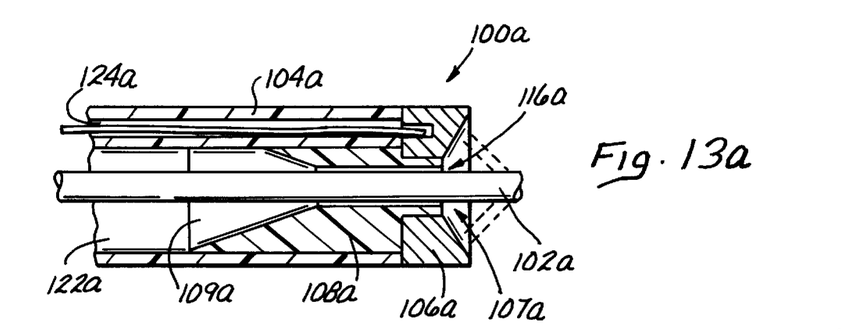
FIG. 13a is a partial longitudinal sectional view of an alternative configuration for the distal end of the second embodiment of the bipolar vascular sealing probe of the present invention.

In the alternative configuration shown in FIG. 13a, the probe 100a comprises a probe body 104 which is a dual-lumen catheter or tube having a first lumen 122a and a second lumen 124a extending longitudinally therethrough. Insulating plug member 108a is inserted in the distal end of the probe body 104a. Proximal electrode wire 120a extends longitudinally through the second lumen 124a and is connected to the proximal electrode 106a which is positioned on the distal end of the probe body 104a. A guide wire passage bore or aperture 116a extends longitudinally through the insulative plug member 108a and through the center of the proximal electrode 106a, as shown. A tapered or frusto conical region 109a is formed on the proximal end of the guide wire bore or aperture 116a to facilitate location and passage of the distal end of the electrode-guide wire 102a through the guide wire bore or aperture 116a. In the alternative configuration shown in FIG. 13a the proximal electrode 106a is a generally round disc-like conductive member having a concave or indented distal face 107a. When the electrode-guide wire 102a is positioned such that the non-insulated region 110a thereof is adjacent the concave or indented distal face 107a of the proximal electrode 106a electrical current will be passed between the non-insulated region 110a of the electrode-guide wire 102a and the concave or indented distal face 107a of the proximal electrode 106a as indicated by dotted line shown on FIG. 13a.

Figure 13B:
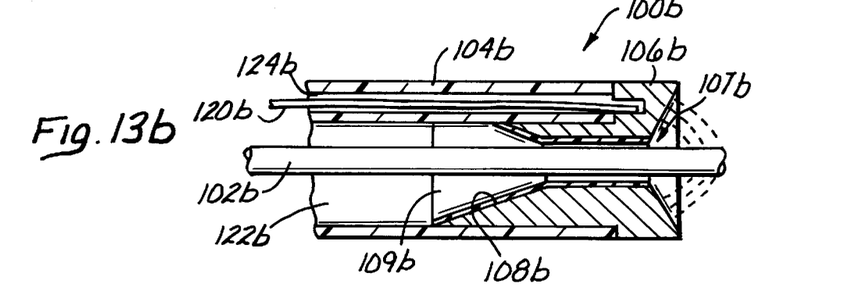
FIG. 13b is a partial longitudinal sectional view of another alternative configuration of the distal end of the second embodiment of a bipolar vascular sealing probe of the present invention.

In the alternative configuration shown in FIG. 13b the probe 100b comprises a probe body 104b formed of a dual-lumen catheter or tube having a first lumen 122b and a second lumen 124b extending longitudinally therethrough. The proximal electrode 106b comprises a generally cylindrical conductive member having a proximal cylindrical portion which inserts into the distal portion of the first lumen 122b of the probe body 104b, and a disc-like distal portion which abuts against the distal end of the probe body 104b, and which has an outer diameter substantially equivalent to the outer diameter of the probe body 104b so as to reside in flush abutment therewith. The insulative plug member 108b comprises an insulated sheath or coating disposed on the inner surface of the guide wire passage bore or aperture 116b which extends longitudinally through the proximal electrode member 106b. A tapered or frusto conical region 109b is formed in the proximal end of the guide wire passage bore or aperture 116b to facilitate location and passage of the distal end of the electrode-guide wire 102b through the electrode-guide wire passage bore or aperture 116b. The proximal electrode member 106b has a concave or indented distal face 107b such that, when the non-insulated region 100b of the electrode-guide wire 102b is positioned adjacent the distal end of the probe 104b, electrical current may pass between the concave or indented distal face 107b of the proximal electrode 106b and the non-insulated region 100b of the electrode-guide wire 102b, as indicated by dotted line shown on FIG. 13b.

The proximal electrode wire 102b extends through the second lumen 124b of the probe body 100b and is connected to the disc-like distal portion of the proximal electrode member 106b, as shown.

Figure 13C:
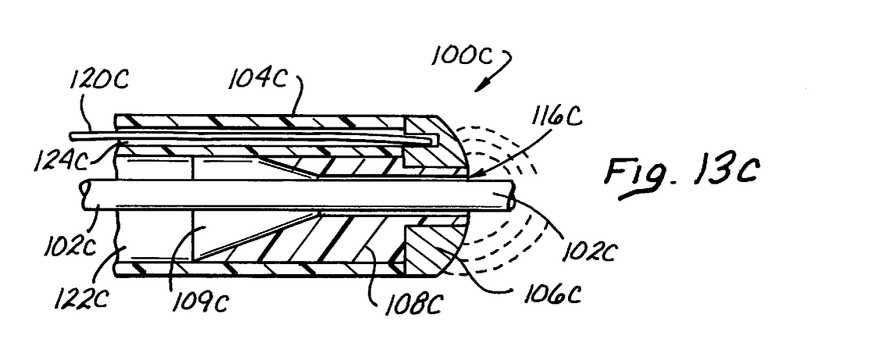
FIG. 13c is a partial longitudinal sectional view of another alternative configuration of the distal end of the second embodiment of a bipolar vascular sealing probe of the present invention.
Figure 13D:
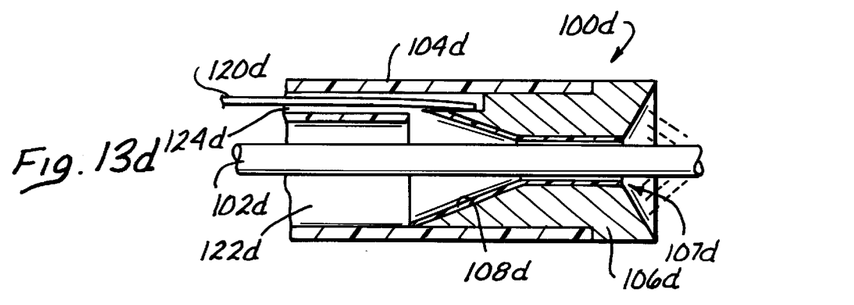
FIG. 13d is a partial longitudinal sectional view of another alternative configuration of the distal end of the second embodiment of a bipolar vascular sealing probe of the present invention.

In the alternative configuration shown in FIG. 13c, the probe 100c comprises a probe body 104c formed of a dual-lumen tube or pliable catheter having a first lumen 122c and a second lumen 124c extending longitudinally therethrough. Insulative plug member 108c is inserted into the distal end of the probe body 104c. Proximal electrode member 106c is mounted on and affixed to the distal end of the probe body, in contact with the insulative plug member 108c, as shown. In this configuration, the proximal electrode member 106c has a convex or distally out-sloping frontal surface 111.

Although the invention has been described herein with reference to the presently preferred embodiments and examples, it will be appreciated that various other embodiments and examples may also be arrived at without departing from the intended spirit and scope of the invention. For example, blood vessel sealing probes of the type and configuration described herein, and which may incorporate the position-facilitating locator apparatus or notch as described herein, may be modified to perform the intended closing of the blood vessel wall puncture site by other than electrocoagulation or resistant heating means, such as a laser or other light-emitting source which will cause the desired heating of the surrounding tissue thereby coagulating or cauterizing the blood vessel wall puncture site in the manner described herein as being produced by the resistance heating or electrocauterization (e.g., monopolar or bipolar) probe tip. Accordingly, it is intended that all such alternative embodiments and examples be included within the scope of the following claims.

What is claimed is:

1. A bipolar vascular sealing probe device for sealing a puncture in a blood vessel comprising the combination of:
   a) a probe comprising:
      an elongate probe body having a proximal end, a distal end and a guide wire passage lumen extending through at least a portion of said probe body;
      a first bipolar electrode formed on said probe body comprising an electrically conductive member positioned near the distal end of said probe body and having a distal face portion which is concave;
      a first conduction pathway extending longitudinally through said probe to carry electrical current from the proximal end of said probe body to said first bipolar electrode; and
   b) an electrode-guide wire device comprising:
      an elongate guide wire having a proximal end, a distal end and an outer surface;
      a second bipolar electrode formed on a discrete distal region of the outer surface of said guide wire;
      a second conduction pathway extending longitudinally through said guide wire to carry electrical current to said second bipolar electrode formed thereon;
      wherein said guide wire being passable through the guide wire passage lumen of said probe such that a portion of said guide wire protrudes out of said guide wire passage lumen, and further such that said second bipolar electrode is located in sufficient proximity to said first bipolar electrode such that electrical current may pass between said first bipolar electrode and said second bipolar electrode.

2. A bipolar vascular sealing probe device comprising the combination of:
   a) a probe comprising:
      an elongate probe body having a proximal end and a distal end;
      a first bipolar electrode formed on said probe body at a first location;
      a first conduction pathway extending longitudinally through said probe to carry electrical current from the proximal end of said probe body to said first bipolar electrode;
      a guide wire passage lumen extending longitudinally through at least a portion of said probe body and opening through a guide wire passage aperture in the distal end of said probe body; and
   b) an electrode-guide wire device comprising:
      an elongate guide wire having a proximal end, a distal end and an outer surface, said guide wire being formed of electrically conductive material and having an electrically insulative coating formed on the outer surface thereof, except for an uncoated region located a spaced-distance from the distal end of the guide wire, said uncoated region forming a second bipolar electrode, and;
      a second bipolar electrode formed on at least a region of the outer surface of said guide wire;
      a second conduction pathway extending longitudinally through said guide wire to carry electrical current to said second bipolar electrode formed thereon;

wherein said guide wire being passable through the guide wire passage lumen of said probe such that a portion of said guide wire protrudes out of said guide wire passage aperture in the distal end of said probe body, and further such that said second bipolar electrode is located in sufficient proximity to said first bipolar electrode such that electrical current may pass between said first bipolar electrode and said second bipolar electrode.

3. The device of claim 2 wherein the guide wire passage lumen formed in said probe is a monorail type lumen which extends through only a distal portion of the probe body.

4. The device of claim 2 wherein said guide wire passage lumen formed in said probe is an over-the-wire type lumen which extends longitudinally through the entire probe body.

5. The device of claim 2 wherein said probe body has a length of 15–150 cm and a diameter of 4–13 French.

6. The device of claim 2 wherein said electrode-guide wire device comprises an elongate guide wire having a length of 15–300 cm and a diameter of 0.014–0.038 inches.

7. The device of claim 2 wherein said first bipolar electrode comprises an electrically conductive band positioned about the outer surface of said probe body.

8. The device of claim 7 wherein said electrically conductive band is positioned on the distal end of said probe body and wherein an electrically insulative plug member, having a disc portion formed on the distal end thereof, the disc portion of said insulative plug member and said electrically conductive band having outer diameters which are substantially equivalent to one another, said disc-portion of said insulative plug member thereby forming an electrically insulative distal end on said probe body, distal to said first bipolar electrode, and wherein said guide wire passage lumen extends through said electrically insulative plug member.

9. The device of claim 2 wherein said first bipolar electrode comprises an electrically conductive member positioned on the distal end of said probe body.

10. The device of claim 9 wherein said electrically conductive member has a distal face portion which is concave.

11. The device of claim 9 wherein said electrically conductive member has a distal face portion which is convex.

12. The device of claim 9 wherein said guide wire passage lumen extends through said electrically conductive member, and wherein an electrically insulative lining is disposed within the portion of said guide wire passage lumen which extends through said electrically conductive member.

13. The device of claim 2 wherein said probe further comprises:

a locator apparatus formed in said probe body at a spaced distance from the distal end of said probe body, said locator apparatus being operative to sense when said locator apparatus is in contact with a blood vessel wall puncture site, thereby indicating that further movement of the probe by a distance equal to said spaced distance will result in positioning of the distal end of said probe adjacent said blood vessel wall puncture site.

14. The device of claim 13 wherein said locator apparatus comprises a locator notch.

15. The device of claim 14 wherein said probe body has a longitudinal axis, and wherein said locator notch comprises:

a) an annular shoulder surface formed in said probe body, said shoulder surface being in a plane which is substantially perpendicular to the longitudinal axis of said probe body; and, b) a tapered region of said probe body located immediately proximal to said abutment shoulder, said tapered region being of gradually narrowed cross sectional dimension.

* * * * *